United States Patent [19]

Smith et al.

[11] Patent Number: 4,861,340
[45] Date of Patent: Aug. 29, 1989

[54] HAND-HELD PNEUMATIC POWER ASSISTED SYRINGE

[75] Inventors: Kevin W. Smith, Miami; Charles R. Slater, Fort Lauderdale, both of Fla.

[73] Assignee: Cordis Corporation, Miami, Fla.

[21] Appl. No.: 258,396

[22] Filed: Oct. 17, 1988

[51] Int. Cl.⁴ .......................................... A61M 37/00
[52] U.S. Cl. ................................................. 604/141
[58] Field of Search ..................... 604/68, 70, 71, 140, 604/141, 143, 146

[56] References Cited

U.S. PATENT DOCUMENTS 3,688,765  9/1972  Gasaway .............................. 604/70
4,093,108  6/1978  Hein et al. ........................... 604/146

Primary Examiner—Jerome L. Kruter
Attorney, Agent, or Firm—Tarolli, Sundheim & Covell

[57] ABSTRACT

A hand-held manually operable-pneumatic power assisted syringe serves for injection of fluids. The syringe includes a barrel-shaped housing having a piston slidably mounted therein between the distal and proximal ends of the housing and dividing the housing into a fluid chamber at the distal end and a gas chamber at the proximal end. A nozzle is mounted on the distal end of the housing and is provided with a discharge passageway for discharging fluid from the fluid chamber as the piston is displaced toward the distal end. A piston push rod extends form the piston and is slidable through an end cap mounted on the proximal end of the housing with the push rod serving to displace the piston in the distal direction. The push rod is hollow and has a first passageway at a location adjacent the piston for communication with the gas chamber and a second passageway at a location exterior of the housing for communication with a source of pressurized gas to thereby fill the gas chamber with pressurized gas. A valve assembly is carried by the push rod and includes a bobbin slidably mounted within the push rod between a normal valve closed position for blocking the second passageway to a valve open position for permitting gas to flow through the second passageway into the push rod and then to the gas chamber.

18 Claims, 4 Drawing Sheets

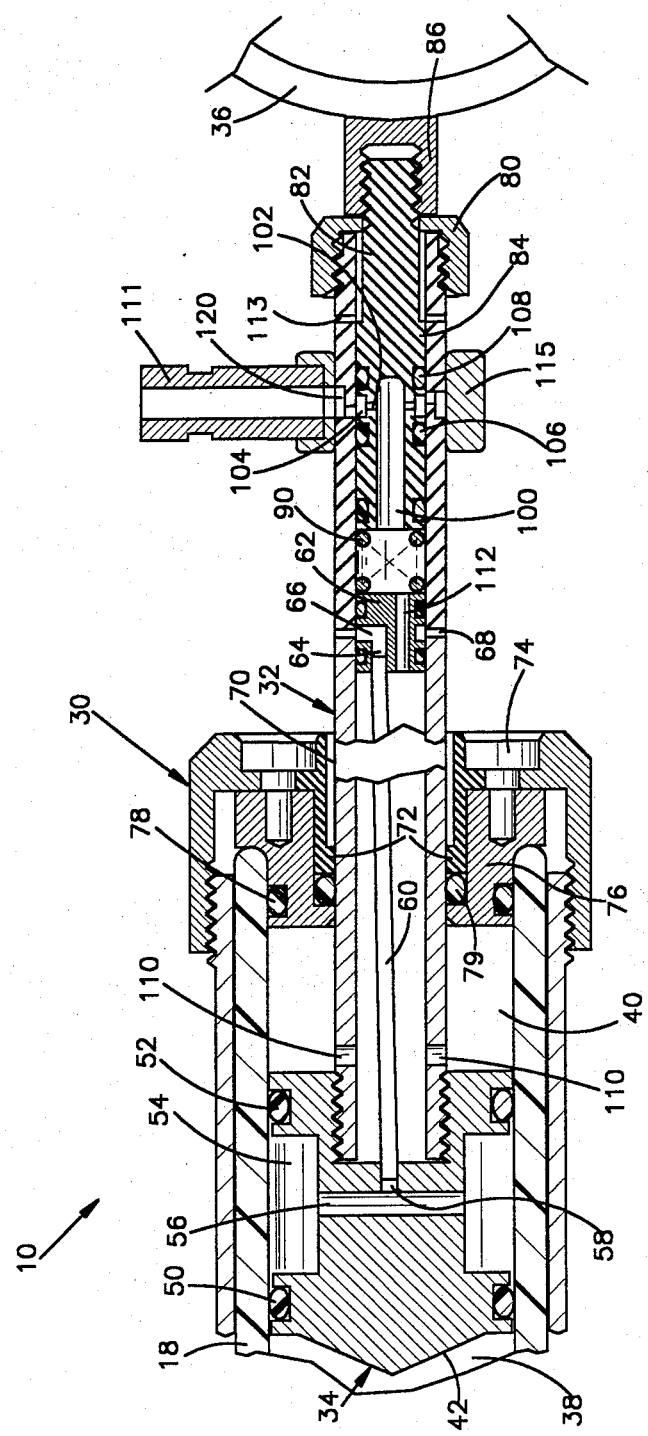

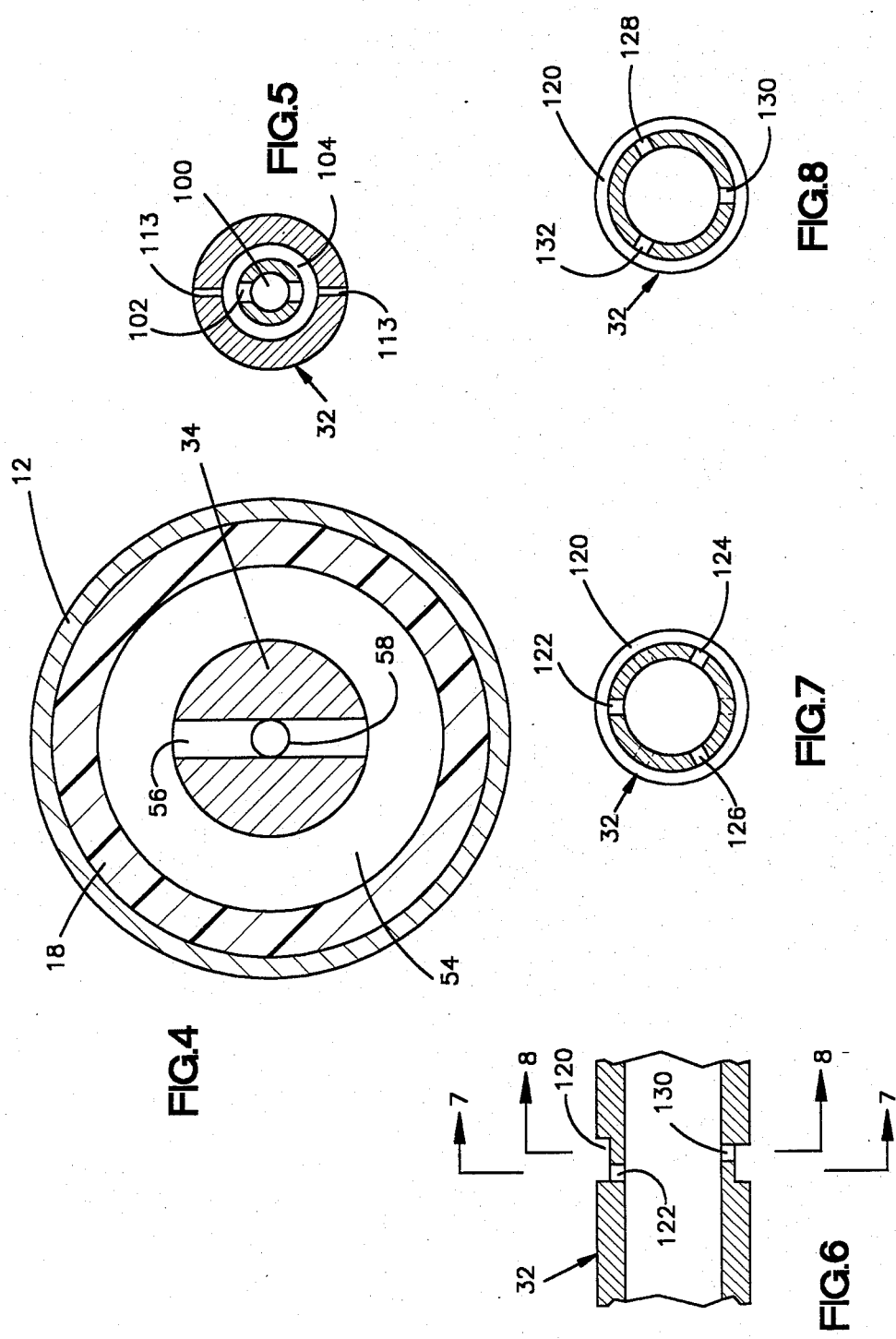

HAND-HELD PNEUMATIC POWER ASSISTED SYRINGE

BACKGROUND AND FIELD OF THE INVENTION

The present invention relates to syringes and, more particularly, to a hand-held pneumatic power assisted syringe for injection of fluid.

One application of the present invention is the injection of contrast media through small-diameter angiographic catheters and the invention will be described with particular reference thereto. It is to be appreciated, however, that the invention may be employed for other purposes such as the injection of thrombolytic drugs through small diameter infusion catheters. The invention may also be employed for auto-perfusion of a patient's blood through the distal lumen of a balloon dilatation catheter during balloon inflation to reduce ischemia. The invention may also be employed for inflating angioplasty and valvuloplasty dilatation balloons. Another application may include the injection of contrast media through the distal lumen of balloon dilatation catheters to visualize the distal vessels in angioplasty. Another application may be the injection of contrast media through the guiding catheter in an angioplasty procedure with the balloon dilatation catheter in place. Another application may be the injection or infusion of other drugs and medications, such an anti-tumor drugs through small infusion catheters.

In angiography, for example, a catheter is placed in an appropriate blood vessel and advanced to the site within the circulatory system to be studied. A radio opaque contrast media is injected through the catheter and flows to the distal end of the catheter into the blood vessel. The area within the blood vessel containing the contrast media can be visualized by means of fluoroscopy. The flow rate from the catheter must be equal to or greater than the rate of blood flow within the blood vessel to obtain good opacification. The flow rate from the catheter is dependent upon the pressure exerted upon the proximal end of the catheter, the length of the catheter, the inner diameter of the catheter, and the viscosity of the contrast media to be injected into the blood vessel.

Small diameter catheters are required for entering small vessels or when blood vessels have a tortuous path. Because of the length and small inner diameters of these catheters, difficulties have been encountered in obtaining the pressure needed to produce the flow rate required for good opacification of the area of the blood under investigation. Frequently, the desired flow rate cannot be attained by manual injection as with a typical manually operated syringe.

The present invention provides a hand-held power assisted syringe which may generate sufficient pressure to inject a contrast media or the like through such a catheter to obtain a flow rate which permits good opacification of the vessel being studied.

The U.S. Pat. No. 3,605,745 to M. Hodosh discloses a hydraulic-powered injection system which includes separate pneumatic-hydraulic cylinders which transfer gas pressure to hydraulic pressure to actuate the piston of a syringe. Hodosh does not include a manual control system built into the syringe so that the gas pressure works as an assist to the manual operation of the syringe. Moreover, the device in Hodosh includes a chamber between the drive-fluid chamber and the injectate chamber. The chamber does not communicate with the atmosphere and, hence, is subject to leakage conditions.

The U.S. Pat. No. 4,323,066 to F. Bourdon discloses a manually controlled hydraulic fluid operated syringe for injection of fluids. Bourdon's device operates by having gas pressure balanced on both sides of a piston until the operator pushes on an operating handle. At that time, the gas flow is shut off where it passes through the piston, causing the downstream pressure to drain down to zero through a vent hole. As the downstream pressure bleeds down below the upstream pressure, the piston is driven forward. In this device, gas pressure is being employed even when the piston is not being actuated. Moreover, there is no venting of the gas pressure downstream of the piston for safety purposes. Consequently, a device such as employed by Bourdon can only be used for relatively low gas pressure for power assistance.

SUMMARY OF THE INVENTION

It is an object of the present invention to provide a new and improved manually operated power assisted syringe for injection of fluid and which does not suffer from the disadvantages of the prior art noted above.

In accordance with one aspect of the present invention, a manually operated hand-held power assisted syringe is provided for injection of fluids. The syringe includes an elongated cylindrical barrel-shaped housing having a distal end and a proximal end. A piston is slidably mounted within the barrel and divides the barrel into a fluid chamber and a gas chamber. A nozzle is mounted on the distal end of the barrel and has a discharge passageway for discharging fluid from the fluid chamber when the piston is being displaced toward the distal end. An end cap is mounted on the proximal end of the barrel and has an aperture therein. A push rod slidably extends through the aperture into the gas chamber. At its distal end, the push rod is mounted to the piston. The push rod extends beyond the end cap and is hollow for essentially its entire length. The push rod has a first passageway at a location adjacent the piston and a second passageway located externally of the housing and adjacent the proximal end of the push rod for communication with a source of pressurized gas for filling the gas chamber. A valve assembly is mounted within the push rod and includes a spool bobbin slidably mounted within the push rod. The spool bobbin has normal valve closed position for blocking the second passageway and is slidable to a valve open position for permitting gas from the source of pressurized gas to flow through the second passageway and, thence, through the push rod to fill the gas chamber with pressurized gas. A manually operated means, such as a thumb ring, is coupled to the bobbin for purposes of displacing the bobbin from the normal valve closed position to the valve open position.

In accordance with a further aspect of the present invention, the spool bobbin is resiliently biased such that the resiliency must be overcome by the operator when displacing the bobbin from the closed position to the open position.

In accordance with a still further aspect of the present invention, the spool bobbin has plural ports defined therein in such a manner that when the operator is displacing the spool bobbin from the closed position to the open position, pressurized gas from the gas source enters the spool bobbin through the ports and passes to the gas chamber whereby gas pressure acts against the spool bobbin to provide forces acting against the manual force exerted by the operator to provide a proportional feedback of the injectate rate to the operator.

Still further, in accordance with the present invention, the piston is provided with a fluid trap between its proximal and distal ends so that any leakage into the trap from the gas chamber and the fluid chamber will be accumulated. The fluid trap has means for venting to the atmosphesre.

Still further, in accordance with the present invention, the means for venting the fluid trap to the atmosphere includes a tubular member extending from the piston through the hollow push rod to a vent port in the push rod.

BRIEF DESCRIPTION OF THE DRAWINGS

The foregoing and other objects and advantages of the present invention will become more readily apparent from the following detailed description, as taken in conjunction with the accompanying drawings, in which:

FIG. 3 is a view similar to that of FIG. 2 with the bobbin valve open for filling the gas chamber;

FIG. 4 is an enlarged sectional view taken along line 4—4, looking in the direction of the arrows in FIG. 2;

FIG. 5 is an enlarged sectional view taken along line 5—5, looking in the direction of the arrows in FIG. 2;

FIG. 6 is an enlarged fragmentary sectional view of a portion of the length of the push rod;

FIG. 7 is a sectional view taken along line 7—7, looking in the direction of the arrows in FIG. 6; and FIG. 8 is a sectional view taken along line 8—8, looking in the direction of the arrows in FIG. 6.

DETAILED DESCRIPTION

Figure 1:
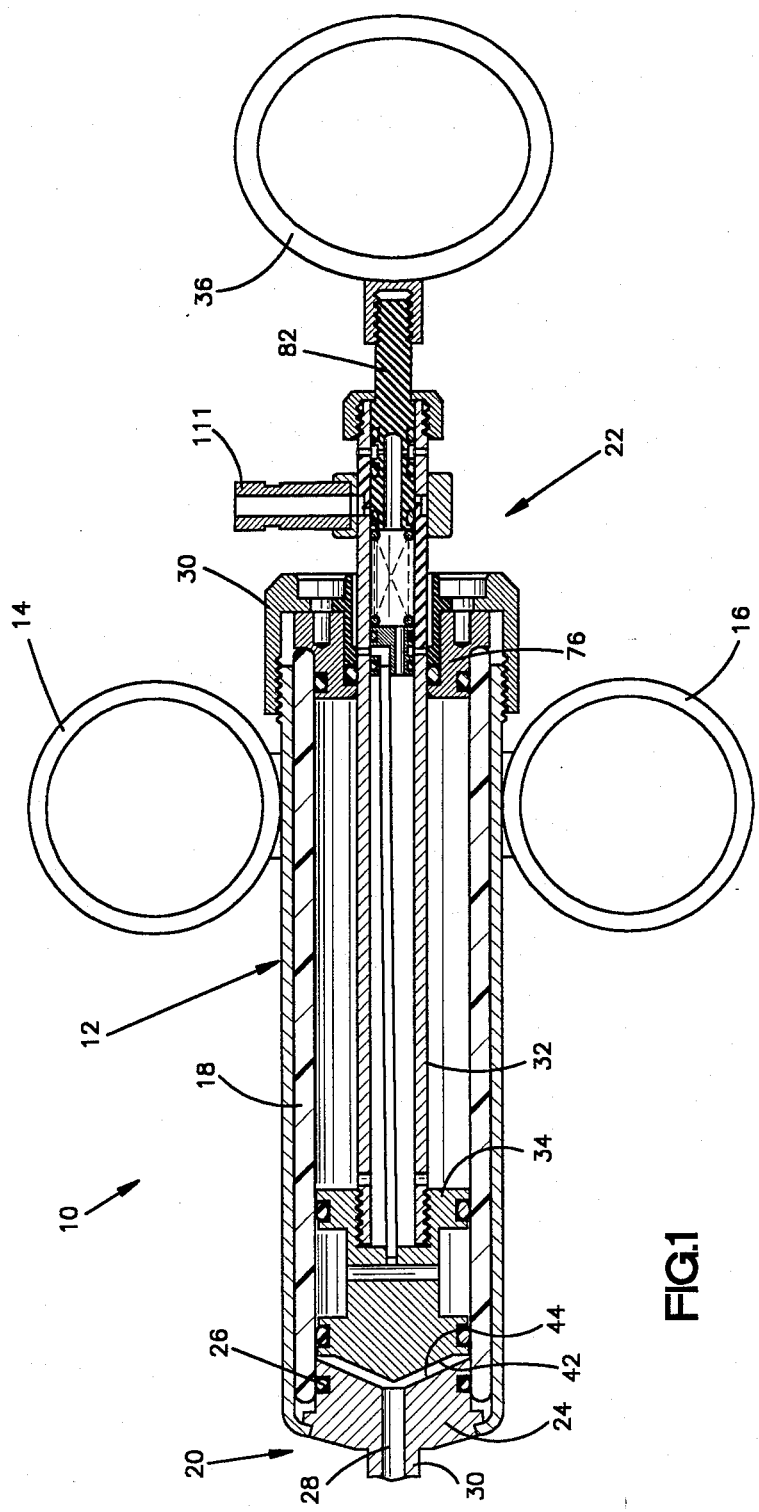
FIG. 1 is a cross sectional view taken along a plane passing through the longitudinal axis of a syringe according to the invention and showing the piston in a fully extended position.
Figure 2:
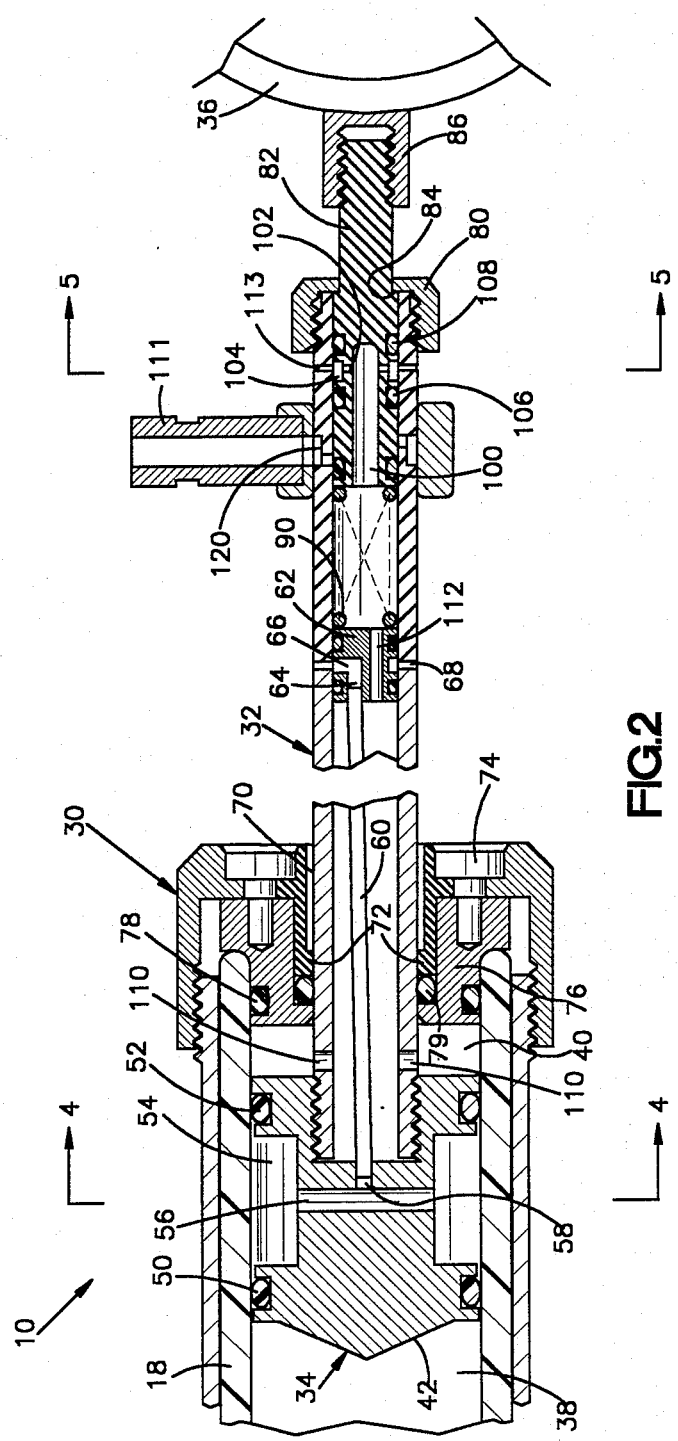
FIG. 2 is a view similar to that of FIG. 1, but showing the piston in its fully retracted position and with the bobbin valve closed.

Reference is now made specifically to FIGS. 1, 2 and 3 which illustrate a preferred embodiment of the invention. As shown, the syringe 10 includes a cylindrical housing 12 constructed of metal, such as stainless steel or nickel-plated brass. The housing 12 has two finger rings 14 and 16 mounted thereon on diametrically opposed sides. Preferably, the housing is provided with longitudinal slots or windows so that the interior may be viewed. The housing envelopes a tubular-shaped syringe barrel 18 which is constructed of a clear, generally transparent plastic material, such as polycarbonate. The syringe 10 has a distal end 20 and a proximal end 22. At the distal end, a nozzle assembly 24 is fitted to the open end of barrel 18 and housing 12 and provides a fluid tight engagement with the barrel by means of a suitable 0-ring 26 mounted in an annular groove in the nozzle assembly 24. A fluid discharge passageway 28 extends through the nozzle assembly 24 and through a shank extension 30. The shank extension 30 is preferably provided with a suitable luer fitting, as is conventional in the art, so that the syringe may be coupled to a suitable catheter for injection of fluid through the passageway 28 and thence through the catheter to the site of interest.

At the proximal end 22, an end cap 30 is secured to the housing 12 by means of internal threads on the cap and external threads on the proximal end of the housing. The end cap 30 has a central aperture which slidably receives an elongated hollow push rod 32. At its distal end, the push rod is threadably secured to a piston 34 and which, in turn, is slidably received within the barrel 18. At its proximal end, the push rod 32 is coupled to a thumb ring 36 which, as will be described in greater detail hereinafter, serves to operate the push rod so as to displace the piston 34 within the barrel 18.

The piston 34 may reciprocate back and forth within the barrel 18 and divides the interior of the barrel into a liquid chamber 38 on the distal side of the piston and a gas chamber 40 on the proximal side of the piston. The forward or distal side of the piston has a tapered wall 42 corresponding with the facing inner wall 44 of the nozzle assembly 24. The piston is circular in cross section and has a pair of longitudinally spaced annular grooves which receive 0-rings 50 and 52 which serve to provide a fluid tight seal separating chambers 38 and 40 during a reciprocation of the piston. The piston has an annular recess 54 formed therein intermediate the O-rings 50 and 52 and which serves as a fluid trap for fluids from chambers 38 and 40.

The piston 42, as viewed in FIGS. 2 and 4, has a vertical bore 56 extending therethrough and which is in communication with a longitudinally extending bore 58. Bore 58, in turn, is secured to one end of a metal tube 60, as by brazing and the like. The metal tube 60 extends through a portion of the length of the hollow push rod 32 and has its opposite end secured, as by brazing, to a vent bobbin 62. The vent bobbin 62 has a passageway 64 extending therein and which is in communication with an annular recess 66 in alignment with diametrically opposed ports 68 extending through the walls of the push rod. This structure provides a means of venting fluids from the fluid trap 54 to the atmosphere. The bobbin 62 is held in place within push rod 32 as with O-rings located in longitudinally spaced annular recesses in the bobbin so that the passageway 64 is held in place in communication with the ports 68.

The fluid venting described above takes place when the push rod is in its fully retracted position, as shown in FIG. 2, as well as when it is in its fully extended position, as shown in FIG. 1. Cap 30 is provided with an oversized bore 70 for slidably receiving the push rod 32. The internal diameter of bore 70, as best seen in FIGS. 2 and 3, is sufficiently oversized that when the push rod is in its extended position, as seen in FIG. 1, an annular passageway is provided between the exterior walls of the push rod and the internal walls of bore 70 to permit fluid to escape from trap 54 by way of tube 60 and the vent ports 68.

Fluids vented into the bore 70 are prevented from leaking into gas chamber 40 by means of the following structure. The bore 70 in end cap 30 is oversized for a portion of its length terminating in an annular collar 72 which just slidably engages the exterior walls of push rod 32. Moreover, the cap 30 is secured, as by rivets 74, to an annular plug 76 which fits into the proximal end of barrel 18 so as to make a very snug fitting therewith. The plug 76 has annular recesses which carry sealing O-rings 78 and 79 in annular passageways defined in the plug. This structure, while permitting slidable movement for the push rod, provides a sealing engagement by means of the O-rings 78 and 79 to prevent leakage of fluids into and out of the gas chamber 40 during operation.

At its proximal end, the push rod 32 is fitted with an end cap 80 which is secured thereto by means of internal threading on the end cap and external threading on the push rod. The end cap 80 has an aperture therein which slidably receives a reduced diameter portion of a spool bobbin 82 which is slidably received within the proximal end of the hollow push rod 32. The spool bobbin 82 has a shoulder 84 which serves as a stop as it abuts a radially inward portion of the end cap 80 preventing the spool bobbin from being displaced in the proximal direction from the push rod as the push rod is extended to its fully retracted position, as is shown in FIG. 2.

The thumb ring 36 is provided with a shank 86 having internal threading which is secured to the proximal end of the spool bobbin 82 by means of external threading on the spool bobbin. The end of shank 86 serves as a stop for limiting the displacement of the spool bobbin in the distal direction, as indicated by the position of the spool bobbin shown in FIG. 3, at which point the end of the shank 86 engages the end cap 80. As will be described, the fully retracted position of FIG. 2 is a valve closed position, and the displaced position of the bobbin, as shown in FIG. 3, is a valve open position.

The valve bobbin 82 is resiliently biased to its normal valve closed position, as shown in FIG. 2, by means of a coil spring 90 located between the stationary vent bobbin 62 and the movable valve bobbin 82.

The movable valve bobbin 82 is an elongated cylindrical body having a bore 100 extending longitudinally through a portion of its length and opening on the distal end thereof. At the proximal end of the bore 100, there is a vertical passageway 102, as best shown in FIG. 5, which extends vertically through the bobbin terminating in an annular recess 104 of a width slightly greater than that of passageway 102. On either side of the annular recess 104, the bobbin carries a pair of O-rings 106 and 108 located in annular recesses which straddle recess 104. With the bobbin in its valve closed position, as shown in FIG. 2, gas in the gas chamber 40 is permitted to vent to the atmosphere through opening 110 in the push rod and thence through the longitudinal passageway 112 in the vent bobbin 62 through the push rod in the area of spring 90 and thence through bore 100 in the bobbin and the vertical bore 102 and through the annular recess 104 and thence through ports 113 at the proximal end of the push rod.

When the bobbin 82 is displaced from its valve closed position, as shown in FIG. 2, to its valve open position, as shown in FIG. 3, the vertical port 102 is displaced so as to be in alignment with a quick disconnect fitting 111. This fitting is adapted to be connected to a source of pressurized gas, such as carbon dioxide. The fitting has a passageway extending therethrough for directing pressurized gas into the bore 100 in bobbin 82 by means of vertical port 102. The fitting 111 is mounted on the exterior of the push rod by means of a collar 115 which coaxially surrounds the push rod and is secured thereto, as by brazing. The push rod 32 has an annular recess 120 which is covered by collar 115.

As best shown in FIGS. 6, 7 and 8, the annular recess 120 in the push rod 32 has two sets of ports extending therethrough in two different planes. In the first plane, as shown in FIG. 7, there are three ports 122, 124 and 126 spaced 120° from each other. The second plane is spaced in the proximal direction, as shown in FIGS. 6 and 8, and has three additional ports 128, 130 and 132 also spaced 120° from each other and rotated relative to that of the ports shown in FIG. 7 by 60°. These ports are of a diameter substantially smaller than the width of annular recess 104 in the bobbin 82. Consequently, as the bobbin 82 is being displaced from its valve closed position, as shown in FIG. 2, toward its valve open position, as shown in FIG. 3, pressurized gas will initially enter bore 100 of the bobbin by way of ports 128, 130 and 132. This gas will flow through bore 100 and thence past the coil spring 90, through bore 112 in the vent bobbin 62, and thence through ports 110 to fill gas chamber 40. This gas pressure will have a tendency to force the bobbin back toward its valve closed position. This provides the operator with a proportional feedback of the injection rate while injecting fluid from the fluid chamber 38 into the patient. This will continue as the operator continues to depress the bobbin with the thumb ring so that as the bobbin reaches the valve open position both sets of ports illustrated in FIGS. 7 and 8 will deliver gas under pressure from the gas source into the bore 100.

As the operator continues to apply force with the thumb ring 36, the shank 86 engages end cap 80 on the push rod and the push rod is then axially displaced in the distal direction. Thus, both manual force and gas pressure cooperate to move the piston 34 toward its fully extended position as shown in FIG. 1 to thereby inject fluid from the fluid chamber into the patient. During this process, compressed gas from the gas chamber 40 is prevented from reaching chamber 38 by means of the O-rings 50 and 52, as well as by the fluid trap 54. The trap 54 is vented to the atmosphere by way of passageways 56 and 58 and thence through the vent tube 60 and passageways 64 and 66 in the vent bobbin 62 and to the atmosphere by way of ports 68. This method of venting the annular trap 54 to the atmosphere also ensures a high pressure differential across the O-rings 50 and 52, further reducing the possibility of leakage of compressed gas into the injectate chamber 38.

In use, the power assisted syringe of the present invention will operate essentially the same as a standard control syringe. Filling the injectate chamber 38 with contrast media or the like will not be affected because the power assisted operation only works in the injection direction. The operator would set the maximum injection pressure in advance by adjusting the supply gas pressure and then use the syringe in the same manner as a standard syringe.

Whereas the invention has been described in conjunction with a preferred embodiment, it is to be appreciated that various modifications may be made within the spirit and scope of the invention as defined by the appended claims.

Having described a preferred embodiment of the invention, we claim:

1. A hand-held manually operable-pneumatic power assisted syringe for injection of fluids, comprising:
   an elongated cylindrical barrel-shaped housing having a distal end and a proximal end;
   a piston slidably mounted within said housing and dividing said housing into a fluid chamber on the distal end of said piston and a gas chamber on the proximal end of said piston;
   a nozzle assembly mounted on the distal end of said housing and having a discharge passageway for discharging fluid from said fluid chamber as said piston is being displaced toward said distal end;

an end cap mounted on the proximal end of said housing and having an aperture therein;

a piston push rod slidably extending through said cap aperture and extending through said gas chamber and having a distal end thereof mounted to said piston for displacing said piston and having a proximal end located beyond the proximal end of said housing, said push rod being hollow for essentially its entire length;

said push rod having a first passageway at a location adjacent to said piston for communication with said gas chamber and a second passageway at a location exterior to said housing adjacent the proximal end of said push rod for communication with a source of pressurized gas for filling said gas chamber with pressurized gas;

valve means carried by said push rod and including first valve means slidably mounted within said push rod and having a normal valve closed position for blocking said second passageway and being slidable to a valve open position for permitting gas to flow through said second passageway and thence through said hollow push rod and to said gas chamber by way of said first passageway; and manually operable means for displacing said first valve means from said valve closed position to said valve open position and for displacing said push rod to move the piston in the distal direction assisted by said gas pressure acting on the proximal end of said piston for injection of fluid from said fluid chamber by way of said nozzle assembly discharge passageway.

2. A syringe as set forth in claim 1 wherein said valve means includes a bobbin slidably mounted within said hollow push rod and means for resiliently urging said bobbin toward its normal valve closed position against any manual force exerted by said manually operated means.

3. A syringe as set forth in claim 2 wherein said bobbin includes a longitudinal bore extending partially through the length of the bobbin and opening in the distal direction, said bobbin having passage means extending radially for communication with said bore so that when said bobbin is in its valve open position gas may enter the bore from the gas supply source and thence through the hollow push rod into said gas chamber.

4. A syringe as set forth in claim 3 wherein said push rod has vent port means extending through the walls of the rod at a location for communication with said bore in said bobbin when said bobbin is in its valve closed position for venting gas within said gas chamber and within said push rod to the atmosphere.

5. A syringe as set forth in claim 4 wherein said vent port means are located adjacent the proximal end of said push rod.

6. A syringe as set forth in claim 3 wherein said push rod has gas port means extending through the walls thereof for communication with said passage means in said bobbin when said bobbin is in its valve open position for communication of gas from a said gas source through the bore of said bobbin and thence into said gas chamber.

7. A syringe as set forth in claim 6 wherein said gas port means includes a plurality of ports extending through the walls of said push rod in such a manner that as the gas from the gas source enters the gas chamber, pressure is applied against the bobbin tending to displace the bobbin in the proximal direction and thereby providing feedback to the operator indicative of the injection rate of fluid being injected from the fluid chamber as the piston is being displaced toward the distal end of the housing.

8. A syringe as set forth in claim 7 wherein said plurality of ports includes ports which are spaced longitudinally from each other so that as the bobbin is being displaced toward its valve open position gas from the gas source enters the bore in said bobbin in a staggered fashion.

9. A syringe as set forth in claim 8 wherein said longitudinally spaced ports include a first plurality of ports and a second plurality of ports with said first and second plurality being respectively located in longitudinally spaced apart planes which planes are transverse to said push rod.

10. A syringe as set forth in claim 9 wherein said planes are parallel and they are perpendicular to the longitudinal direction of said push rod.

11. A syringe as set forth in claim 10 wherein said passage means in said bobbin includes an annular recess having a width which is greater than the diameter of each port in said plurality of ports in said push rod.

12. A syringe as set forth in claim 11 wherein said planes containing said first and second plurality of ports in said push rod are spaced apart by a distance less than the width of said annular recess in said bobbin.

13. A syringe as set forth in claim 1 wherein said piston has a recess formed therein for serving as a fluid trap for trapping fluid therein between said gas chamber and said piston chamber and means for venting said fluid trap to the atmosphere.

14. A syringe as set forth in claim 13 wherein said recess takes the form of an annular recess on said piston intermediate its ends and spaced from the gas chamber and said fluid chamber.

15. A syringe as set forth in claim 14 including passageway means extending through said piston from said annular recess into the interior of said hollow push rod and wherein said means for venting said trap to the atmosphere includes tube means located within said hollow push rod and connecting said passageway means in said piston to the atmosphere.

16. A syringe as set forth in claim 15 wherein said push rod has vent port means extending through the walls thereof and adapted to be connected to one end of said tube means for venting said trap.

17. A syringe as set forth in claim 16 including a vent bobbin mounted within said hollow push rod and having passageway means in registry with the vent port means in said push rod and in communication with one end of said tube means for venting said trap.

18. A syringe as set forth in claim 16 wherein said vent bobbin has a longitudinal passageway extending therethrough for passing gas from said gas source through said hollow push rod.

* * * * *